United States Patent
Liu et al.

(10) Patent No.: US 11,547,780 B2
(45) Date of Patent: Jan. 10, 2023

(54) INDUCER FOR REGENERATION OF BONE AND SOFT TISSUE, AND METHOD FOR MAKING SAME AND USES THEREOF

(71) Applicant: Yingqin Liu, Guangxi (CN)

(72) Inventors: Yingqin Liu, Guangxi (CN); Guangchen Sun, Guangxi (CN); Xin Sun, Guangxi (CN)

(73) Assignee: Yingqin Liu, Guilin (CN)

( * ) Notice: Subject to any disclaimer, the term of this patent is extended or adjusted under 35 U.S.C. 154(b) by 0 days.

(21) Appl. No.: 16/369,246

(22) Filed: Mar. 29, 2019

(65) Prior Publication Data

US 2019/0224381 A1 Jul. 25, 2019

Related U.S. Application Data

(63) Continuation of application No. PCT/CN2017/102270, filed on Sep. 19, 2017.

(30) Foreign Application Priority Data

Oct. 9, 2016 (CN) .......................... 201610878374.2

(51) Int. Cl.

| A61L 27/36 | (2006.01) |
| A61L 27/54 | (2006.01) |
| A61K 38/18 | (2006.01) |
| A61P 19/08 | (2006.01) |
| A61L 27/58 | (2006.01) |
| A61L 27/12 | (2006.01) |
| A61L 27/22 | (2006.01) |
| A61L 27/38 | (2006.01) |
| A61L 27/50 | (2006.01) |

(52) U.S. Cl.
CPC .......... *A61L 27/58* (2013.01); *A61K 38/1875* (2013.01); *A61L 27/12* (2013.01); *A61L 27/22* (2013.01); *A61L 27/227* (2013.01); *A61L 27/36* (2013.01); *A61L 27/365* (2013.01); *A61L 27/3633* (2013.01); *A61L 27/3691* (2013.01); *A61L 27/38* (2013.01); *A61L 27/50* (2013.01); *A61L 27/54* (2013.01); *A61P 19/08* (2018.01); *A61L 2300/112* (2013.01); *A61L 2300/412* (2013.01); *A61L 2300/414* (2013.01); *A61L 2430/02* (2013.01)

(58) Field of Classification Search
CPC ...... A61L 27/36; A61L 27/3633; A61L 27/54; A61K 38/1875; A61P 19/08
See application file for complete search history.

(56) References Cited

U.S. PATENT DOCUMENTS

| 2005/0013872 A1 | 1/2005 | Freyman | |
| 2006/0147433 A1* | 7/2006 | Hiles | A61K 35/37 424/93.7 |
| 2011/0229440 A1* | 9/2011 | Dealy | A61P 19/04 424/93.7 |
| 2013/0172999 A1 | 7/2013 | Kaplan | |
| 2013/0245716 A1* | 9/2013 | Hechavarria | A61N 1/0428 607/50 |
| 2014/0178346 A1 | 6/2014 | Byrne et al. | |
| 2015/0265653 A1 | 9/2015 | Matheny | |

FOREIGN PATENT DOCUMENTS

| CN | 101563450 A | 10/2009 | |
| CN | 102614546 A | 8/2012 | |
| CN | 104922730 A | 9/2015 | |
| CN | 105636598 A | 6/2016 | |
| WO | WO-2015031882 A1 * | 3/2015 | ............. A61L 27/54 |

OTHER PUBLICATIONS

Yu et al., Dev. Biol., 2012, vol. 372(2):263-273.*
Freytes et al., Biomaterials, 2008, vol. 29(11):1630-1637.*
Zhiyong Qu, et al., Practical Hand Surgery [M], People's Military Medical Press, 2003; p. 29-30.
Bin Wang et al., Repair of Hand Tissue Defect [M], People's Military Medical Press, 2008; p. 237-240.
Mohammad KA,Neufeld DA.Bone growth is induced by nail transplantation in amputated proximal phalanges.[J].Calcif Tiss Int, 1999,65:408-410.
Masaki H,Ide H.Regeneration potency of mouse limbs.[J].Dev. Growth Differ.,2007, 49:89-98.
Yu L,Han M,Yan M.et al.BMP signaling induces digit regeneration in neonatal mice.[J].Development.2010,137,551-559.
Yu L,Han M,Yan M,et al.BMP2induces segment-specific skeletal regeneration from digit and limb amputations by establishing a new endochondral ossification center. [J. ] Dev. Biol. 2012, 372:263-273.
Ide H.Bone pattern formation in mouse limbs after amputation at the forearm level.[J].Developmental Dynamics 2012,241:435-441.
Reing JE,Zhang L,MyersIrvin J.et al.Degradation products of extracellular matrix affect cell migration and proliferation. [J].Tissue Eng Part A 2009,15:605-614.
Agrawal V,Johnson SA,Reing J.Epimorphic regeneration approach to tissue replacement in adult mammals.[J]. P. Proc Natl Acad Sci USA 2010, 107:3351-3355.
Agrawal V,Kelly J.Tottey S.et al.An isolated cryptic peptide influences osteogenesis and bone remodeling in an adult mammalian model of digit amputation.[J].Tissue Eng Part A.Dec. 2011; 17(23-24):3033-44.
Hechavarria D,Dewilde A,Braunhut S.et al.Biodome regenerative sleeve for biochemical and biophysical stimulation of tissue regeneration. [J].Medical Engineering and Physics 2010,32(9):1065-1073.

(Continued)

*Primary Examiner* — Xiaozhen Xie

(57) ABSTRACT

An inducer is directed to the induction of in situ regeneration in regenerative medicine. The inducer including an extracellular matrix and/or a bone morphogenetic protein, can induce the regeneration of bone and soft tissues surrounding the bone such as muscle, blood vessel and skin at the residual tissues where trauma occurs. The amount of regenerated tissue is associated with the dose of the implanted inducer.

3 Claims, 6 Drawing Sheets

(56) References Cited

OTHER PUBLICATIONS

Sivak WN, Ruane EJ, Hausman SJ, Rubin JP, Spiess AM. Decellularized Matrix and Supplemental Fat Grafting Leads to Regeneration following Traumatic Fingertip Amputation. Plast Reconstr Surg Glob Open. Oct. 12, 2016; 4(10):e1094.

Kevin C Chung, original, Repair and Construction for Hand and Upper Limb [M], People's Military Medical Press, 2013; p. 87-88.

* cited by examiner

INDUCER FOR REGENERATION OF BONE AND SOFT TISSUE, AND METHOD FOR MAKING SAME AND USES THEREOF

CROSS-REFERENCE TO RELATED APPLICATIONS

This application is a continuation of International Patent Application No. PCT/CN2017/102270, filed on Sep. 19, 2017, which claims the benefit of priority from Chinese Application No. 201610878374.2, filed on Oct. 9, 2016. The contents of the aforementioned applications, including any intervening amendments thereto, are incorporated herein by reference.

TECHNICAL FIELD

The application is directed to induction of in situ regeneration in regenerative medicine. The induced regeneration in the present application is organ regeneration of multiple tissues, including bone tissue regeneration, as well as regeneration of soft tissues around the bone such as muscle, blood vessel and skin. The present invention can be used for regeneration of completely severed tissues (where the isolated original tissue is not available) such as regeneration of severed fingers and limbs, and is also suitable for regeneration of incompletely severed tissues, such as bone defect and nonunion. The present invention relates to an inducer and a composition for inducing regeneration, and methods for making the same and uses thereof.

BACKGROUND

Some lower organisms such as earthworms and leeches have high regenerative capabilities. Complete regeneration of the fore and hind limbs or tails after amputation takes place in some amphibians such as lizards, salamanders and frogs. Mammalians exhibit weak regenerative capability. For a few of mammalians, appendages such as velvet antler can be completely regenerated. The distal phalanges (Phalange 3, P3) of humans and rodent (for example, mice) are capable of incomplete regeneration; that is, regeneration occurs after the amputation of a distal end of P3 but not after the amputation of a proximal end of P3. Other digits, for example the middle phalanges (Phalange 2, P2) and upper and lower limbs after amputation cannot be regenerated. The present invention induces bone generation of damaged tissues with an extracellular matrix (ECM) and a bone morphogenetic protein (BMP), which shows significant effects.

Currently, researches on the regeneration of the severed digits mostly employ the complete severance of toes of mice as a model, including regeneration of severed toes without soft tissues which are more difficult to regenerate. Soft tissue plays an important role in the repair of bone trauma, and bone tissues without soft tissue coating may become necrotic after the bone trauma is healed. Therefore, during the amputation of limbs or digits, the bone needs to be truncated to a length shorter than the soft tissue, such that the bone can be coated by the soft tissue (Zhiyong Qu, et al., Practical Hand Surgery [M], People's Military Medical Press, 2003; Kevin C Chung, original, Repair and Construction for Hand and Upper Limb [M], People's Military Medical Press, 2013). The replanted severed finger should be embedded in the soft tissue of the body to increase the survival rate within 3 weeks after replantation of the severed finger (Bin Wang et al., Repair of Hand Tissue Defect [M], People's Military Medical Press, 2008).

There are three types of inducers for mouse digit regeneration, living tissues (nail bed or germ), growth factors (BMPs, bFGF) and extracellular matrix (ECM). These inducers function in different ways. The living tissues such as nail bed or germ are directly transplanted to a trauma site; the growth factors such as gelatin or blue gelatinous particles containing BMPs are implanted subcutaneously into the wound; and ECM in the form of liquid ECM is injected near the wound or exposed to the wound with a special device. The living tissues can induce the regeneration of various bone tissues such as ulna, radius, carpus and phalange at the forearm (Mohammad K A, Neufeld D A. Bone growth is induced by nail transplantation in amputated proximal phalanges. [J]. Calcif Tiss Int, 1999, 65: 408-410; Masaki H, Ide H. Regeneration potency of mouse limbs. [J]. Dev. Growth Differ, 2007, 49:89-98). BMPs are also effective in the bone regeneration. For example, BMP7/BMP2 can promote the regeneration of the distal phalange (P3) in the case where a proximal end of P3 is amputated which is not regenerative (Yu L, Han M, Yan M. et al. BMP signaling induces digit regeneration in neonatal mice [J]. Development. 2010, 137, 551-559). BMP2 can be used to extend the length of the middle phalange (P2), but cannot promote joint regeneration in the case where P2 is amputated (Yu L, Han M, Yan M, et al. BMP2 induces segment-specific skeletal regeneration from digit and limb amputations by establishing a new endochondral ossification center [J]. Developmental Biology. 2012, 372:263-273). Gelatin containing BMP7 can be used to induce the formation of heterotopic bone in the case where the bones of neonatal mice are removed and soft tissues such as skin are remained (Ide H. Bone pattern formation in mouse limbs after amputation at the forearm level [J]. Developmental Dynamics. 2012, 241: 435-441). ECM shows the weakest bone regeneration effect, but ECM degradation products can promote the migration of various progenitor/stem cells to the wound of mouse digits (Reing J E, Zhang L, Myers Irvin J. et al. Degradation products of extracellular matrix affect cell migration and proliferation [J]. Tissue Eng Part A 2009, 15: 605-614; Agrawal V, Johnson S A, Reing J. Epimorphic regeneration approach to tissue replacement in adult mammals [J]. Proc Natl Acad Sci, 2010, USA 107:3351-3355). Some unknown proteins extracted from ECM can induce the formation of a small amount of callus (Agrawal V, Kelly J, Tottey S. et al. An isolated cryptic peptide influences osteogenesis and bone remodeling in an adult mammalian model of digit amputation [J]. Tissue Eng Part A. 2011 December; 17 (23-24): 3033-44). In addition, the liquid ECM combines with electrical stimulation to induce regeneration of mouse digits (Hechavarria D, Dewilde A, Braunhut S. et al. Biodome regenerative sleeve for biochemical and biophysical stimulation of tissue regeneration [J]. Medical Engineering and Physics 2010, 32(9): 1065-1073), and the ECM powder is used for the regeneration of severed fingers in human in combination with adipose tissue; however, there is no description about new bone formation (Sivak W N, Ruane E J, Hausman S J, Rubin J P, Spiess A M. Decellularized Matrix and Supplemental Fat Grafting Leads to Regeneration following Traumatic Fingertip Amputation. Plast Reconstr Surg Glob Open. 2016 Oct. 12; 4(10):e1094). There are some reports about the induction of ECM in pig bladder on the regeneration of severed digits, but the occurrence of bone regeneration still remains uncertain. ECM is used as a tissue engineering scaffold material for the repair of various soft tissues, but there is still a lack of strong evidence to demonstrate the role of ECM in bone tissue regeneration. It can be seen from the above that these inducers in the prior art have the following defects: the living tissue reducers have limited sources and immune rejection; BMPs are expensive and can only induce the regeneration of limited bone mass; and the amount of the regenerated tissue induced by ECM extracts is too small.

At present, there is an urgent need to improve the inducer for regeneration, especially bone regeneration.

SUMMARY

The present application aims to induce bone regeneration of the severed digits without regenerative capability; or to convert incomplete regeneration of distal phalanges into complete regeneration; or to achieve regenerative repair of other bone defect or nonunion, especially the regeneration of bone without soft tissue (such as severed digits), for both new and old wounds.

It has been found for the first time that ECM plays an important role in the bone regeneration of severed toes. The applicant found that the regenerated toes induced by ECM are significantly different from the control, and the regenerated bone mass is comparable to that induced by Bead+BMP in high concentration (500 μg/mL of BMP). It has also been surprisingly found that compared to the control, the increased regenerated bone mass by the combination of ECM and BMP is significantly higher than the sum of regenerated bone mass by ECM and BMP alone, indicating significant synergy of ECM and BMP (see Example 2, FIGS. 4 and 5). Furthermore, the amount of the regenerated bone increases as the BMP concentration increases, and even BMP and ECM in medium or low concentration can induce excess bone regeneration. It has further been surprisingly found that the inducer of the invention is significantly effective in the regeneration of bones without soft tissues (such as severed toes). Additionally, ECM has a variety of sources and can be readily applied to clinical promotion. Therefore, the inducer of the invention can reduce the cost while improving the amount and quality of bone regeneration.

In an aspect, the application provides an inducer.

1. In an embodiment, the inducer comprises an ECM as a main ingredient, wherein the ECM is derived from animal tissues or organs. ECM includes, but is not limited to extracellular matrixes from small intestine, trachea, bladder and bone.

2. In an embodiment, the inducer comprises an ECM as a main ingredient, wherein the ECM is derived from non-animal tissues or organs.

3. In an embodiment, the inducer comprises an ECM as a main ingredient, wherein the ECM derived from animal or non-animal tissues or organs according to 1 or 2 is treated by a physical or chemical method, including but not limited to lyophilization, pulverization, degradation, cross-linking, gelation and 3D-printing modeling.

4. In an embodiment, the inducer comprises BMP as a main ingredient, wherein the BMP is a member of BMP superfamily, including but not limited to: BMP-2, BMP-3, BMP-3B/GDF-10, BMP-4, BMP-5, BMP-6, BMP-7/OP-1, BMP-8/OP-2, BMP-8B, BMP-9, BMP-10, BMP-11, BMP-12, BMP-13, BMP-14, CDMP-1, CDMP-2, CDMP-3, GDF-1, GDF-2, GDF-3, GDF-4, GDF-5/CDMP-1/BMP-14, GDF-6/CDMP-2/BMP-13, GDF-7/CDMP-3/BMP-12, GDF-8 and GDF-9.

5. In an embodiment, the BMP of the inducer according to 4 is derived from, for example bone matrix gelatin or an extract containing BMP.

6. In an embodiment, the inducer comprises BMP as a main ingredient, wherein the BMP may be replaced with an exogenous additive exerting bone formation by means of BMP, including but not limited to: BMP binding proteins such as Follistatin and active substances producing BMP proteins.

7. In an embodiment, the inducer comprises BMP as a main ingredient, wherein the BMP is characterized by a peptide chain of a core sequence of the protein according to 4, 5 or 6.

8. In an embodiment, the inducer comprises BMP as a main ingredient and an auxiliary, wherein the auxiliary includes, but is not limited to: pure water, a neutral buffer and an inorganic salt containing ions such as calcium, phosphorus or magnesium.

9. In an embodiment, the inducer is for external use, and the inducer functions by implantation into a lesion of a tissue and is completely absorbed during the regeneration.

10. In an embodiment, the inducer comprises ECM according to 1, 2 or 3 and BMP according to 4, 5, 6 or 7 as main ingredients.

11. In an embodiment, an inducer is composed of:
a. an extracellular matrix (ECM);
b. a bone morphogenetic protein (BMP); and
c. a diluent of BMP.

In an aspect, the application provides a regeneration inducer comprising an extracellular matrix (ECM) and/or a bone morphogenetic protein (BMP).

In some embodiments, the regeneration inducer comprises the extracellular matrix and/or the bone morphogenetic protein as a main ingredient.

In some embodiments, the regeneration inducer comprises the extracellular matrix and the bone morphogenetic protein as main active ingredients.

In some embodiments, the regeneration inducer comprises the extracellular matrix and the bone morphogenetic protein as the only active ingredients.

In some embodiments, the extracellular matrix is derived from animal tissues or organs, including but not limited to: small intestine, trachea, bladder and bone.

In some embodiments, the extracellular matrix is derived from non-animal tissues or organs.

In some embodiments, the extracellular matrix is treated by physical or chemical methods, including but not limited to: lyophilization, pulverization, degradation, cross-linking, gelation and 3D-printing modeling.

In some embodiments, the bone morphogenetic protein is a member of BMP superfamily including but not limited to: BMP-2, BMP-3, BMP-3B/GDF-10, BMP-4, BMP-5, BMP-6, BMP-7/OP-1, BMP-8/OP-2, BMP-8B, BMP-9, BMP-10, BMP-11, BMP-12, BMP-13, BMP-14, CDMP-1, CDMP-2, CDMP-3, GDF-1, GDF-2, GDF-3, GDF-4, GDF-5/CDMP-1/BMP-14, GDF-6/CDMP-2/BMP-13, GDF-7/CDMP-3/BMP-12, GDF-8 and GDF-9.

In an embodiment, the BMP of the inducer is derived from, for example bone matrix gelatin or an extract containing BMP.

In an embodiment, the inducer comprises BMP as a main ingredient, wherein the BMP may be replaced with an exogenous additive exerting bone formation by means of BMP, including but not limited to: BMP binding proteins such as Follistatin and active substances producing BMP, such as a transgenic product expressing BMP.

In some embodiments, the bone morphogenetic protein further comprises a peptide chain having a core sequence of the BMP superfamily and the BMP binding protein.

In some embodiments, the regeneration inducer further comprises an auxiliary, including but not limited to, phosphate, acetate, trehalose, hydroxyapatite micropowder, glucose, sorbitol, pure water, ethanol, phosphate buffer, acetate buffer and citrate buffer.

In some embodiments, the auxiliary is a diluent. The diluent may be optionally added with an inorganic salt or other osteogenic components, including but not limited to an inorganic salt containing calcium, phosphorus or magnesium. The diluent includes, but is not limited to, pure water, phosphate buffer, acetate buffer and citrate buffer, preferably pure water or a neutral buffer.

In some embodiments, the diluent is a phosphate buffer containing 5% of trehalose.

In some embodiments, the phosphate buffer is at pH of 7.2.

In some embodiments, the regeneration inducer further comprises hydroxyapatite micropowder as the auxiliary.

In some embodiments, a dry weight ratio of hydroxyapatite micropowder to ECM is 100:1-1:10,000, for example, 100:1-1:1000, 10:1-1:200, 5:1-1:100, 2:1-1:50 and 1:10-1:50.

In some embodiments, the regeneration inducer is composed of an extracellular matrix, a bone morphogenetic protein and an auxiliary.

In some embodiments, the regeneration inducer is composed of an extracellular matrix, a bone morphogenetic protein and a diluent.

In some embodiments, the regeneration inducer is for external use, and the inducer functions by implantation into a lesion of a tissue and is partially or completely absorbed during the regeneration.

In some embodiments, a dry weight ratio of BMP to ECM in the regeneration inducer is 100:1-1:1,000,000, for example, 10:1-1:1,000,000, 1:100-1:1,000,000, 1:100-1:100,000, 1:1,000-1:1,000,000, 1:1,000-1:100,000, 1:2,000-1:100,000, 1:4,000-1:70,000 or 1:5,000-1:50,000. The dry weight ratio of BMP to ECM in the regeneration inducer may be, for example 1:1,000, 1:2,000, 1:3,000, 1:4,000, 1:5,000, 1:6,000, 1:7,000, 1:8,000, 1:9,000, 1:10,000, 1:20,000, 1:30,000, 1:40,000, 1:50,000, 1:60,000 or 1:70000.

In some embodiments, the regeneration inducer includes 0.0001%-100% by weight of ECM and BMP, for example, 0.01%-99%, 0.1%-95%, 0.5%-90%, 1%-85%, 2%-80%, 5%-70%, 10%-90%, 30%-90%, 40%-90%, 0.001%-90%, 0.01%-90% or 0.1%-90%, specifically such as 0.0001%, 0.001%, 0.01%, 0.1%, 0.2%, 0.5%, 1%, 2%, 3%, 4%, 5%, 6%, 7%, 8%, 9%, 10%, 20%, 30%, 40%, 50%, 60%, 70%, 80%, 90%, 95%, 99% or 100%

In some embodiments, the regeneration inducer is used to induce bone regeneration in a subject.

In some embodiments, the regeneration inducer is used to induce bone regeneration without soft tissue in a subject.

In some embodiments, the regeneration inducer is used to induce bone regeneration of a severed digit or limb without regenerative capability in a subject.

In some embodiments, the regeneration inducer is used to convert incomplete regeneration of a distal phalange of a subject to complete regeneration.

In some embodiments, the regeneration inducer is used for regenerative repair of bone defect/nonunion in a subject.

In some embodiments, the severed digits or limbs without regenerative capability are severed toes, fingers or limbs with soft tissues.

In some embodiments, the severed digits or limbs without regenerative capability are free of soft tissues.

In some embodiments, the regeneration inducer is used for bone regeneration of a severed distal end of a distal phalange in a subject.

In some embodiments, the regeneration inducer is used for bone regeneration of a severed proximal end of a distal phalange in a subject.

In some embodiments, the regeneration inducer is used for bone regeneration of a severed middle phalange in a subject.

In another aspect, the application provides a composition of BMP and ECM.

In some embodiments, a dry weight ratio of BMP to ECM in the composition is 100:1-1:1,000,000, for example, 10:1-1:1,000,000, 1:100-1:1,000,000, 1:100-1:100,000, 1:1000-1:1,000,000, 1:1000-1:100,000, 1:2000-1:100,000, 1:4000-1:70,000 or 1:5,000-1:50,000. The dry weight ratio of BMP to ECM in the combination of the invention may also be, for example, 1:1,000, 1:2,000, 1:3,000, 1:4,000, 1:5,000, 1:6,000, 1:7,000, 1:8,000, 1:9,000, 1:10,000, 1:20,000, 1:30,000, 1:40,000, 1:50,000, 1:60,000 or 1:70,000.

In some embodiments, the composition of BMP and ECM is used to induce bone regeneration in a subject.

In some embodiments, the composition of BMP and ECM is used to induce bone regeneration in a subject without soft tissues.

In some embodiments, the composition of BMP and ECM is used to induce bone regeneration of severed digits or limbs without regenerative capability in a subject.

In some embodiments, the composition of BMP and ECM is used to convert incomplete regeneration of a distal phalange into complete regeneration in a subject.

In some embodiments, the composition of BMP and ECM is used for regenerative repair of bone defect/nonunion in a subject.

In some embodiments, the severed digits or limbs are severed digits or limbs with soft tissues.

In some embodiments, the amputated digits or limbs are free of soft tissues. In some embodiments, the composition is used for bone regeneration of a severed distal end of a distal phalange in a subject.

In some embodiments, the composition is used for bone regeneration of a severed proximal end of a distal phalange in a subject.

In some embodiments, the composition is used for bone regeneration of a severed middle phalange in a subject.

In another aspect, the application further provides a use of the regeneration inducer or the composition in the preparation of a drug for bone regeneration in a subject.

In some embodiments, the invention includes a use of the composition of the invention as the only active ingredient in the preparation of a drug for bone regeneration in a subject.

In some embodiments, the bone regeneration is performed without soft tissues.

In some embodiments, the subject is a mammal, a bird, a fish, or a reptile.

In some embodiments, the subject is a mammal.

In some embodiments, the subject is selected from a cat, a dog, a sheep, a goat, a cow, a horse, a pig, a mouse, a rat or a cavy.

In some embodiments, the subject is a human.

In some embodiments, the bone regeneration is used for a severed digit or limb without regenerative capability.

In some embodiments, the bone regeneration refers to complete regeneration converted from the incomplete regeneration of the phalanges.

In some embodiments, the bone regeneration refers to regenerative repair of bone defect/nonunion.

In some embodiments, the severed digits or limbs are severed digits or limbs with soft tissues.

In some embodiments, the amputated digits or limbs are free of soft tissues.

In some embodiments, the bone regeneration is used for a severed distal end of a phalange in a subject.

In some embodiments, the bone regeneration is used for a severed proximal end of a phalange in a subject.

In some embodiments, the bone regeneration is used for a severed middle phalange in a subject.

In another aspect, the application further provides a method for bone regeneration at a lesion in a subject, comprising: exposing the regeneration inducer or the composition of the invention to the lesion of the subject.

In some embodiments, the bone regeneration is performed without soft tissues.

In some embodiments, the subject is a mammal, a bird, a fish or a reptile.

In some embodiments, the subject is a mammal.

In some embodiments, the subject is selected from the group consisting of a cat, a dog, a sheep, a goat, a cow, a horse, a pig, a mouse, a rat, and a cavy.

In some embodiments, the subject is a human.

In some embodiments, the lesion refers to a severed digit or limb without regenerative capability.

In some embodiments, the bone regeneration refers to complete regeneration converted from the incomplete regeneration of the distal finger/digit into.

In some embodiments, the lesion part refers to a part of bone defect/nonunion.

In some embodiments, the severed digits or limbs are severed digits or limbs with soft tissues.

In some embodiments, the severed digits or limbs are free of soft tissues.

In some embodiments, the bone regeneration is used for a severed distal end of a phalange in a subject.

In some embodiments, the bone regeneration is used for a severed proximal end of a phalange in a subject.

In some embodiments, the bone regeneration is used for a severed middle phalange in a subject.

Preparation of Inducers

In another aspect, the application provides a method for preparing the regeneration inducer, comprising:

mixing BMP with ECM.

In some embodiments, the method for preparing the regeneration inducer of the invention further comprises: mixing BMP or ECM with an auxiliary before mixing ECM with BMP.

In some embodiments, the method for preparing the regeneration inducer comprises:

(1) dilution: diluting BMP with a diluent; and
(2) mixing: mixing the diluted BMP solution with ECM.

In some embodiments, in step (1), BMP is diluted with the diluent to a concentration of 0.01-10,000 μg/mL, for example, 0.05-5,000 μg/mL, 0.1-2,000 μg/mL, 1-1,000 μg/mL, 0.05-500 μg/mL, 0.1-500 μg/mL, 0.5-500 μg/mL, 1-500 μg/mL, 30-500 μg/mL, 100-1,000 μg/mL, 200-800 μg/mL, 250-700 μg/mL or 300-600 μg/mL.

In some embodiments, in step (2), a dry weight ratio of BMP to ECM is 100:1-1:1,000,000, for example, 10:1-1:1,000,000, 1:100-1:1,000,000, 1:100-1:100,000, 1:1,000-1:1,000,000, 1:1,000-1:100,000, 1:2,000-1:100,000, 1:4,000-1:70,000, or 1:5,000-1:50,000; specifically, 1:1,000, 1:2,000, 1:3,000, 1:4,000, 1:5,000, 1:6,000, 1:7,000, 1:8,000, 1:9,000, 1:10,000, 1:20,000, 1:30,000, 1:40,000, 1:50,000, 1:60,000 or 1:70,000.

In some embodiments, in step (2), a weight ratio of the BMP solution to ECM is 100:1-1:1,000, for example, 10:1-1:100, 1:10-1:100, 5:1-1:50, 5:1-1:10, or 2:1-1:5; specifically, 2:1, 1:1, 1:2, or 1:3.

In some embodiments, the method further comprises: step (3) modeling the mixture in step (2) into a shape of a bone to be regenerated.

In some embodiments, a gel/semigel inducer for use is obtained in step (3) of the method.

In some embodiments, the method further comprises: step (4) drying the inducer obtained in step (3).

In some embodiments, the method further comprises: optionally adding an auxiliary before, after or when mixing BMP with ECM, where the auxiliary include, but is not limited to inorganic salts, preferably hydroxyapatite micropowder.

In some embodiments, the diluent includes, but is not limited to pure water, phosphate buffer, acetate buffer and citrate buffer, preferably pure water or a neutral buffer.

In some embodiments, the diluent is a phosphate buffer containing 5% of trehalose.

In some embodiments, the phosphate buffer is at pH of 7.2.

In some embodiments, a dry weight ratio of the hydroxyapatite micropowder to ECM is 100:1-1:10,000, for example 10:1-1:200, 5:1-1:100, 2:1-1:50, 1:10-1:50.

In some embodiments, the preparation needs to be performed under a clean and sterile environment, and individual components of the inducer are required to be sterilized prior to preparation.

In an embodiment, the application provides a method for preparing an inducer, where the inducer is composed of:

a. an extracellular matrix (ECM);
b. a bone morphogenetic protein (BMP); and
c. a diluent of the bone morphogenetic protein (BMP).

The method for preparing an inducer comprises or consists of:

(1) dilution: diluting the bone morphogenetic protein with the diluent to a concentration of 0.01-1,000 μg/mL;

(2) mixing: mixing the extracellular matrix, the diluted bone morphogenetic protein solution and optionally, an auxiliary, where a mixing ratio of the diluted bone morphogenetic protein solution to the extracellular matrix is 1:1-1:100,000, for example 1:1-1:1,000;

(3) modeling: modeling the mixture obtained in step (2) into a shape of the bone to be regenerated to prepare the inducer; and (4) performing under a clean and sterile environment, and sterilizing individual components of the inducer prior to preparation.

Beneficial Effects of the Inducer of the Invention:

The P2 (middle phalange) amputation experiment in mice shows that in the case where the amputated original tissues are discarded, the inducer can induce the regeneration of both of bone and soft tissues such as muscle and skin at the stump of the amputated toes, thus increasing the length and the thickness of the residual toes. The regenerated bone tissue has a pore structure with an uneven surface. Over time, the pore structure in the regenerated bone is reduced and the bone surface tends to be smooth.

It should be understood that the terminologies used herein are merely for illustration, but are not intended to limit the scope of the invention.

Unless otherwise specified, all of the technical terms used herein have the same meaning as commonly understood by those skilled in the art.

Definition

Terms "BMP" and "bone morphogenetic protein" may be used interchangeably herein and pertain to the BMP superfamily, including but not limited to BMP-2, BMP-3, BMP-3B/GDF-10, BMP-4, BMP-5, BMP-6, BMP-7/OP-1, BMP-8/OP-2, BMP-8B, BMP-9, BMP-10, BMP-11, BMP-12, BMP-13, BMP-14, CDMP-1, CDMP-2, CDMP-3, GDF-1, GDF-2, GDF-3, GDF-4, GDF-5/CDMP-1/BMP-14, GDF-6/CDMP-2/BMP-13, GDF-7/CDMP-3/BMP-12, GDF-8 and GDF-9.

Sources of the BMP are not limited. For example, it can be obtained by a genetic engineering method (e.g., recombination of human BMP); or obtained using BMP-containing materials such as bone tissue, decalcified bone and bone matrix gelatin; or obtained in the form of pure BMP or an extract containing BMP, for example, from materials such as bone tissue, decalcified bone and bone matrix gelatin by means of purification or the like.

Terms "extracellular matrix", "ECM" and the like may be used interchangeably herein and refer to, in a narrow sense, a collagen-rich material found in cells of animal tissues and used as a structural element in tissues. It typically involves a complex mixture of polysaccharides and proteins secreted by the cells. The extracellular matrix can be separated and treated in various ways. The extracellular matrix (ECM) can be isolated from animal tissues or organs. The animal includes mammals, for example, domestic or farm animals such as cats, dogs, sheep, goats, cows, horses and pigs, and primates; birds; and laboratory animals such as mice, rats and cavies. The animal tissues or organs include, but are not limited to, small intestine, trachea, bladder, bone, small intestinal submucosa, gastric submucosa, bladder submucosa, tissue mucosa, dura, liver basement membrane, pericardium. The extracellular matrix is often obtained after isolation and treatment. Generally, the extracellular matrix includes an extracellular matrix derived from non-animal tissues or organs, such as an artificial extracellular matrix and a cell-derived extracellular matrix cultured in vitro. Preferably, the extracellular matrix may be prepared according to the methods described in Agrawal V, Johnson S A, Reing J. Epimorphic regeneration approach to tissue replacement in adult mammals. [J]. Proc Natl Acad Sci, 2010, USA 107:3351-3355.

Term "subject" includes mammals, for example, domestic or farm animals such as cats, dogs, sheep, goats, cows, horses and pigs; humans and primates; birds; laboratory animals such as mice, rats and cavies; fishes; and reptiles; preferably humans.

Term "regeneration" refers to a repair process, where after an entirety, tissue or organ of a living body is partially lost or damaged due to trauma, a structure with identical or similar shape and function to the lost or damaged portion is formed on the basis of the remaining portion.

Term "bone regeneration" refers to bone tissue regeneration. Generally, the bone regeneration involves the regeneration of bone tissue as well as soft tissues around the bone such as muscles, blood vessels, and skin. Only the repair of soft tissues cannot be defined as bone regeneration. The bone regeneration of the invention includes, but is not limited to bone regeneration without and with soft tissues, regeneration of a severed digits or limbs (with or without regenerative capability; and with or without soft tissues); complete regeneration converted from incomplete regeneration of the phalange; and regenerative repair of bone defect/nonunion. The bone regeneration of the invention particularly refers to in situ bone regeneration, and more particularly bone regeneration without soft tissue.

Term "bone regeneration without soft tissues" means that in the regeneration of the severed digits or limbs, all tissues distal to the bone cross section are missing or removed; and in other bone defects, all soft tissues coating the severed bone are missing or removed. The above regeneration involves the regeneration of both of bone and soft tissues, and the regenerated soft tissues include skin.

Terms "inducer" and "regeneration inducer" may be used interchangeably herein and refers to a composition which induces regeneration of tissues and/or organs in a subject, particularly a composition for inducing bone regeneration.

Term "non-regenerative" means that organs, tissues or the like of a living body do not have the ability to regenerate in a natural state in which no external inducing factor is introduced.

Term "auxiliary" refers to a substance other than the active ingredients (e.g., ECM and/or BMP) added during the preparation or formulation of the pharmaceutical preparation. The auxiliary may be liquid, solid or gaseous, and may be a single substance or a mixture of various substances. The auxiliary includes filler, stabilizer, antibiotic, antioxidant, preservative and diluent. The auxiliary is known to those skilled in the art, including but not limited to hydroxyapatite micropowder, phosphate, acetate, trehalose, glucose, sorbitol, pure water, ethanol, phosphate buffer, acetate buffer, and citrate buffer. More information about auxiliaries may be referred to the reference books in the art, for example, "Summarization of Pharmaceutical Adjuvant" (Sichuan Science and Technology Press, $2^{nd}$ edition) edited by Luo Mingsheng and Gao Tianhui.

Term "diluent" refers to a liquid for diluting BMP and/or ECM, for example, an organic or inorganic solvent, such as water, ethanol or a mixture thereof. The diluent may be optionally added with an inorganic salt or other osteogenic components, including, but not limited to, an inorganic salt containing calcium, phosphorus or magnesium. The diluent of the invention includes, but is not limited to pure water, phosphate buffer, acetate buffer, and citrate buffer, preferably pure water or a neutral buffer, such as a phosphate buffer containing 5% of trehalose (pH=7.2).

Term "composition" refers to a composition in the form of dosage unit or a kit for combined administration, where BMP and ECM can be administered independently at the same time or separately at a time interval, especially when BMP and ECM are allowed to be administered in combination to show combined action such as synergy. The term "composition" used herein includes a "fixed composition", which means that BMP and ECM are administered simultaneously to a subject as a single entity or preparation, including a product obtained by mixing or combining BMP, ECM and optional auxiliaries, also called combination product.

Administration

The inducer of the invention can be formulated into any appropriate preparations and administered via any suitable routes. The inducer may be prepared into a form of solution, suspension, emulsion, and lyophilized preparation for injection; gel, ointment, cream, suppository, and patch for topical administration; and aerosol, spray, and powder for topical administration. Preferably and generally, the inducer is topically administered to the sites that need bone regeneration; and more preferably, the inducer of the invention functions by implantation into the lesion of the tissue and is completely absorbed during the regeneration.

The middle toe was not amputated, while the toes (index toe and ring toe) at both sides of the middle toe were amputated at the second toe ridges of the index and ring toes (as indicated by the arrow). The third toe ridge of the middle toe was flush with the second toe ridges of the index and ring toes (as indicated by the arrow), so the third toe ridge of the middle toe can be used as a reference coordinate for the regeneration length of index and ring toes. Circled numbers 1 and 2 indicate the amputation positions.

Figure 1:
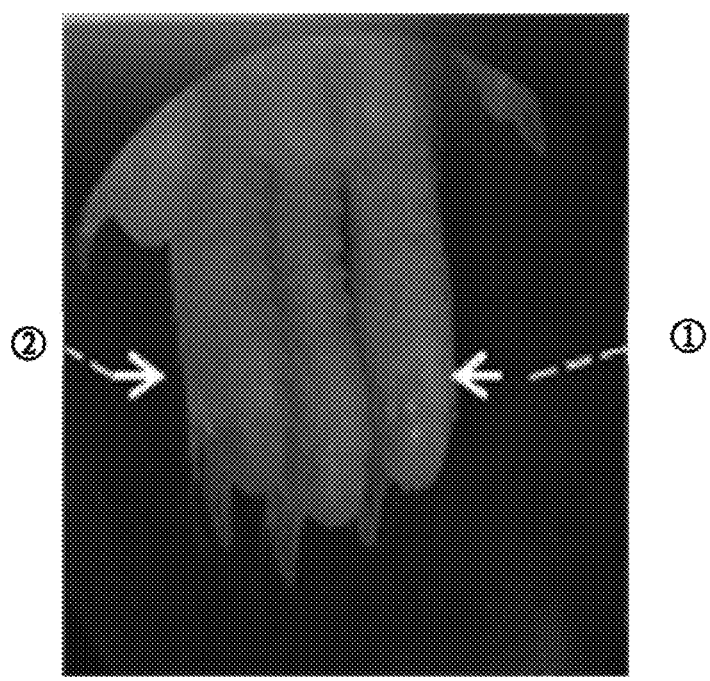
FIG. 1 shows a picture of a normal mouse toe (ventral side, i.e., palm side).
Figures 1, 2:
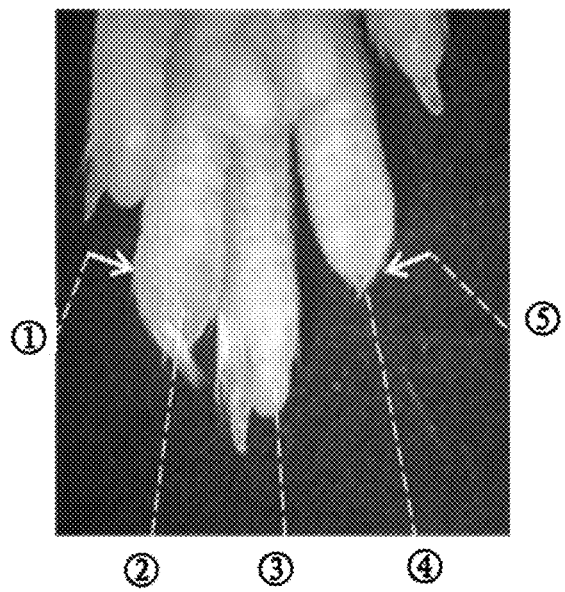
Figure 2:
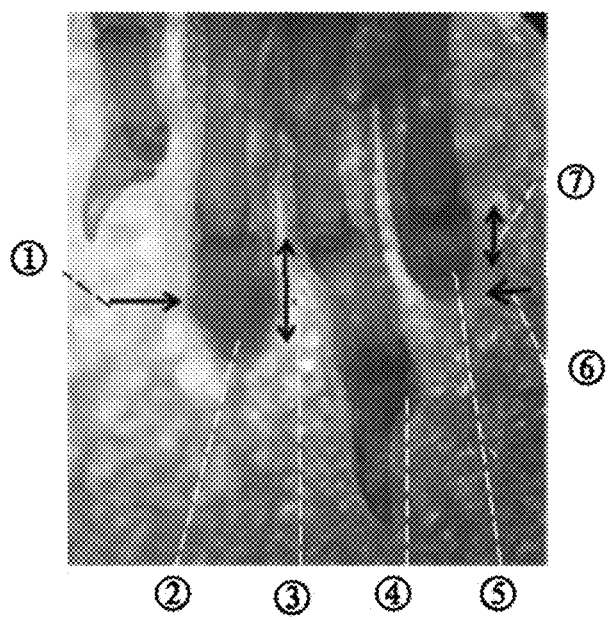

FIGS. 2-1 and 2-2 show pictures of mouse middle phalange (P2) 35 days after amputation and a transparent specimen thereof.

FIGS. 2-1 shows a picture of mouse middle phalange (P2).

FIGS. 2-2 shows a picture of a transparent specimen.

The index toe was implanted with an inducer and the right toe (index toe) was used as a control without inducer. The transparent specimen was used to observe the bone. The single arrow indicates the amputation position and the double arrow indicates the length of P2. The length of the phalange implanted with inducer was twice that of the control phalange. FIGS. 2-1 and 2-2 refer to the same sample, and the ECM gel was used alone as the inducer. In FIG. 2-1: circled number 1: amputation position of the toe implanted with the inducer; circled number 2, regenerated toe through inducer implantation after amputation; circled number 3, normal toe (middle toe) without damage; circled number 4, control toe without inducer implantation after the amputation; and circled number 5, amputation position of the control toe. In FIG. 2-2: circled number 1, amputation position of the toe implanted with the inducer; circled number 2, regenerated toe through inducer implantation after amputation; circled number 3, length of the regenerated P2 bone; circled number 4, normal toe (middle toe) without damage; circled number 5, control toe without inducer implantation after amputation; circled number 6, amputation position of the control toe; and circled number 7, length of P2 bone of the control toe.

Figures 1, 3:
Figures 2, 3:
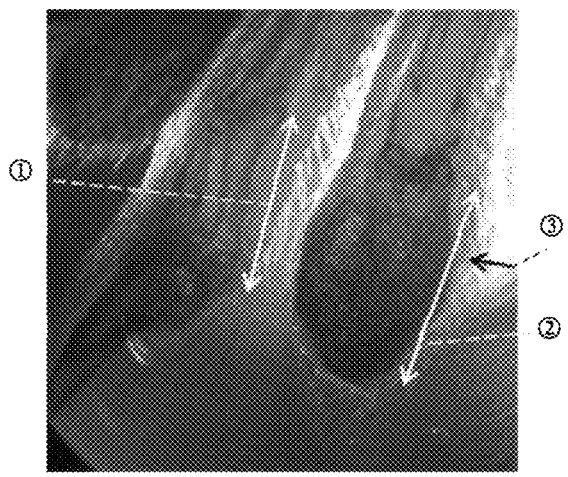
Figure 3:
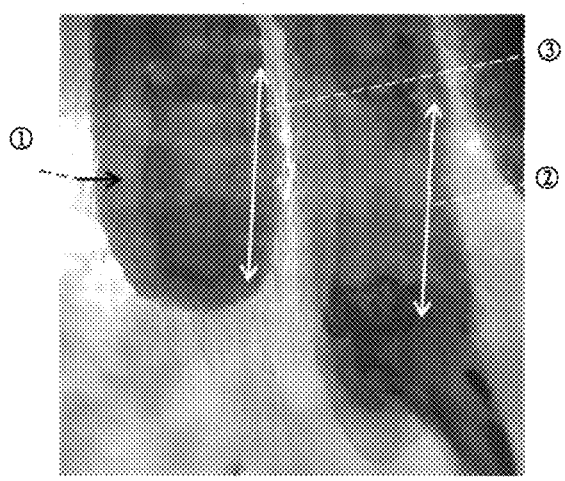

FIGS. 3-1, 3-2 and 3-3 show micro-CT imaging and transparent specimen images of over-regenerated mouse P2 (different samples).

FIG. 3-1 shows a micro-CT image (50 days after amputation);

FIG. 3-2 shows a transparent specimen image (34 days after amputation); and

FIG. 3-3 shows another transparent specimen image (35 days after amputation).

The length of the regenerated P2 phalange was substantially equal to that of P2 of the normal middle toe, and the thickness of the regenerated toe was equal to or greater than that of the normal middle toe. The normal middle toe of mouse was substantially equal to the middle finger of the human, where P2 is the longest. The above results indicated that the bone mass of the regenerated P2 was greater than that of the original P2, which showed excessive regeneration of the mouse toe. A single arrow indicates the amputation position and a double arrow indicates the length of the P2. In FIG. 3-1: circled number 1, amputation position of the toe implanted with the inducer; circled number 2, regenerated P2; circled number 3, P3 bone of the normal middle toe; and circled number 4, P2 bone of the normal middle toe. In FIG. 3-2, circled number 1, length of the P2 bone of the normal middle toe; circled number 2, length of the regenerated P2 bone; and circled number 3, amputation position of the toe implanted with the inducer. In FIG. 3-3, circled number 1: amputation position of the toe implanted with the inducer; circled number 2, length of the P2 bone of the normal middle toe; and circled number 3, length of the regenerated P2 bone.

Figure 4:
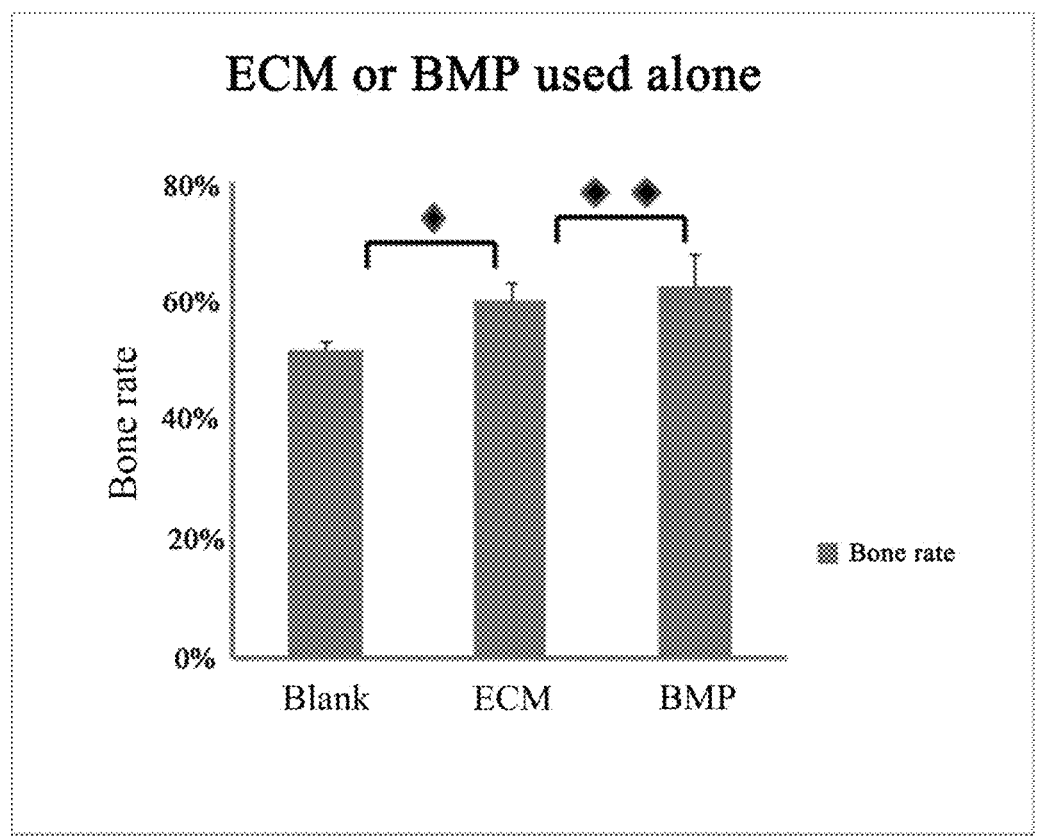

FIG. 4 shows comparison of regenerative efficacies of the blank group, ECM alone group and BMP alone group. ♦ indicates p<0.05 for T test (p=0.011 for the ECM alone group vs. the blank group, and p=0.041 for the BMP alone group (500 μg/mL) vs. the blank group), ♦♦ indicates p>0.05 for T test (p=0.908 for the ECM alone group vs. the BMP alone group).

Figure 5:
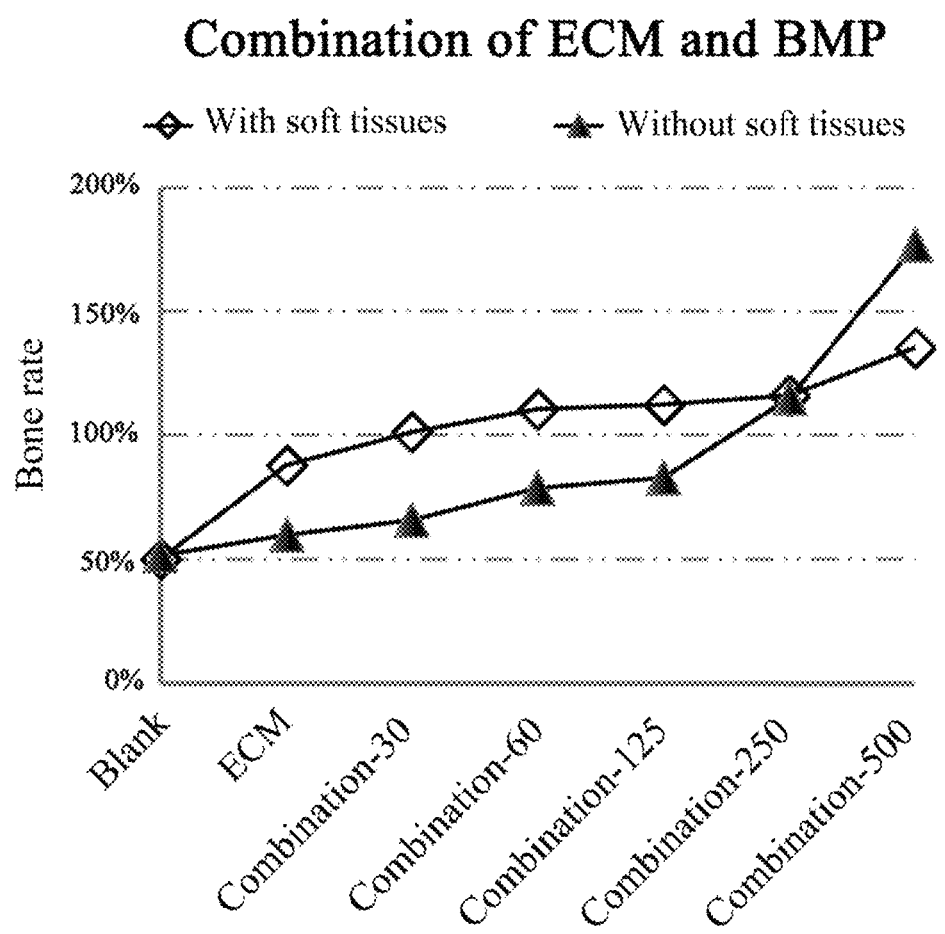

FIG. 5 shows comparison of regenerative efficacies of blank, ECM alone, combination of ECM and BMP for the amputated toe with soft tissues and the amputated toe without soft tissues. Combination-30 is a combination of ECM and 30 μg/mL of BMP, and the rest are named in the same way.

Figure 6:
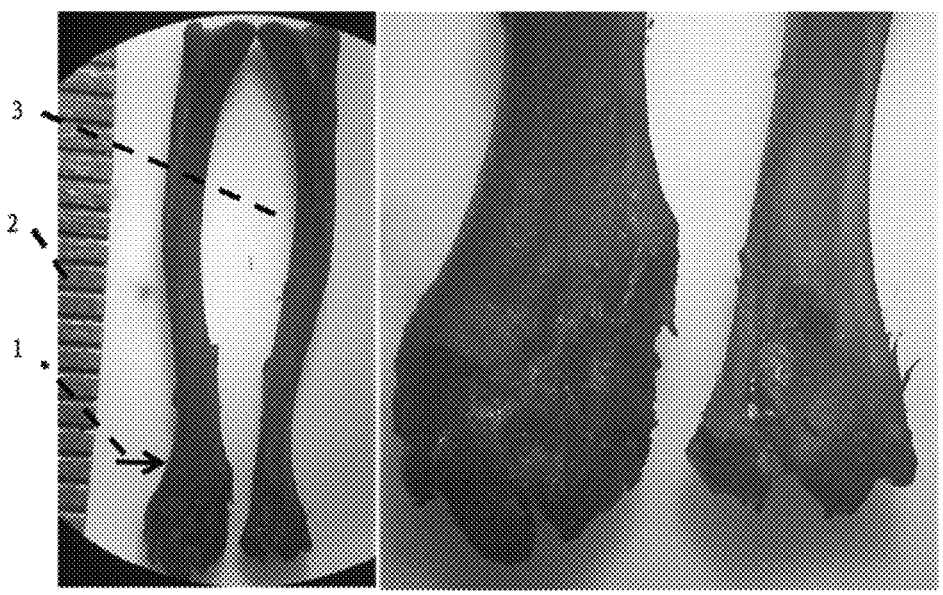

FIG. 6 shows regenerative effect after amputation of the mouse tibia. The right picture shows a partial enlarged view of the left picture. In FIG. 6, number 1, amputation position of the mouse tibia (proximal end of ankle); number 2, a millimeter scale; and number 3, normal tibia.

DETAILED DESCRIPTION OF EMBODIMENTS

The following embodiments are used to illustrate the invention in detail, but are not intended to limit the scope of the invention as defined by the appended claims.

Example 1

1. ECM was obtained from a fresh pig bladder and prepared into an ECM lyophilized powder according to a published method (Agrawal V, Johnson S A, Reing J. Epimorphic regeneration approach to tissue replacement in adult mammals [J]. Proc Natl Acad Sci, 2010, USA 107: 3351-3355). The ECM lyophilized powder was dispersed in a humid environment with humidity greater than 85%, so that it was affected with damp and hydrated to prepare an ECM gel.

2. Recombinant human protein BMP-2 was purchased from Peprotech Inc. (Catalog #120-2). The BMP-2 was diluted to 100 μg/mL with a diluent to prepare a BMP-2 solution. Diluent for BMP-2 was a phosphate buffer (pH=7.2) containing 5% of trehalose.

3. Use methods of an amputated toe model and an inducer:

Toes at both sides of a hind limb of a mouse were amputated at the distal second toe cross striation (middle of P2 bone), so that all tissues distal to the amputation surface were separated and removed. The inducer prepared as the above method was implanted into a wound to expose to the damaged bone tissue.

4. Method and result

The ECM gel and the BMP-2 solution were mixed in an appropriate weight ratio to produce a mixture. The mixture was modeled and implanted into the stump of the mouse toe amputated at P2. In this example, the ECM gel was used at a dose of 0.25 mg/per toe (dry weight) and the BMP solution was used at amount of 0.25 μL/per toe, where a dry weight ratio of the BMP to the ECM was 1:10,000. After 35 days, length of the regenerated P2 was greater than that of the original P2; thickness of the regenerated P2 was equivalent to that of the original P2; and the bone mass of the regenerated P2 was more than that of the original P2, thereby showing excessive regeneration of the mouse digit. The results were shown FIGS. 1-3.

Example 2

2.1 Measurement (Bone Rate) of Regenerated Amount by the Inducer

The mouse P2 bone amputation experiment showed that in the case where the amputated original tissues were removed, the inducer could induce synchronous regeneration of bone and soft tissues such as muscle and skin at a stump of the amputated toe, thereby increasing the length and the thickness of the amputated toe. The regenerated bone tissue had a pore structure and an uneven surface. Over time, the pore structure in the regenerated bone was reduced, and the bone surface tended to be smooth.

Bone regeneration was a sign to determine whether regeneration occurred at the amputated toe, therefore, the regeneration effect used herein was expressed by relative bone mass, which was temporarily called "bone ratio" (see formula 1). In formula 1, the non-damaged toe was the middle toe, which corresponded to the middle finger of human, and the regenerated toes were toes at both sides of and adjacent to the middle toe, which corresponded to the index finger and the ring finger of human. The amputation position of the mouse toe was the middle of P2 bone of the toes at both sides (the index toe and ring toe), which corresponded to the second toe cross striation of the toes at both sides or the third toe cross striation of the middle toe of the body surface (see FIG. 1). The adult Kunming mouse without damage had a P2 bone ratio of 0.926 (i.e., the normal bone ratio was 0.926). The regeneration mass hereinafter was expressed by "bone rate", which was a percentage obtained from the bone ratio through 0.926 (normal bone ratio)-normalization (see formula 2). For example, the normal bone rate is 100% in the case of no loss (=normal bone ratio÷0.926×100%).

bone ratio=P2 bone mass of the regenerated digit÷P2 bone mass of the digit without damage     Formula 1:

bone rate=bone ratio÷0.926×100%     Formula 2:

(i.e., bone rate=P2 bone mass of the regenerated digit÷P2 bone mass of the digit without damage÷0.926×100%)

2.2 Regeneration of Amputated Toes Without Soft Tissues

In this model, bones and soft tissues of the toes at both sides of the middle toe of on the mouse hind limbs were amputated at the middle of the P2 bone, so that all the tissues distal to the amputation surface were separated and removed. Four days after the amputation, when the wound was naturally closed, the inducer was implanted into the wound to expose to the residual section of the P2 bone. Thereafter, no treatment was performed until the mice were sacrificed 35 days after the implantation and the samples were collected for analysis. Used herein all were adult Kunming mice, each group of 3 mice, and 2 toes of the left and right limbs of each mouse were amputated, i.e., a total of 12 toes were amputated in each group.

A blue gel bead group (Affi-Gel Blue Gel beads, purchased from Bio-Rad company, Hercules, Calif.), i.e., BMP alone group, was designed to compare the regenerative effects of ECM and BMPs according to a literature (Yu L, Han M, Yan M, et al. BMP2 induces segment-specific skeletal regeneration from digit and limb amputations by establishing a new endochondral ossification center. [J]. Developmental Biology. 2012, 372: 263-273). Concentration of BMP was 500 µg/mL, and diameter of the selected bead was 0.4 mm, so that more than 16.7 ng of the BMP can be carried (administration amount of the BMP in the combination-125 group was 15.6 ng/per toe). The ECM alone group indicated the absence of the BMP, where ECM was used at amount of 0.25 mg/per toe (dry weight). A group where toes at both sides were not implanted with an inducer after the amputation was called the blank group. The average bone rates of the blank group, ECM alone group and BMP alone group were 51.7%, 60.0% and 62.5%, respectively (see FIG. 4). P values obtained through comparison of the ECM alone group and the blank group and comparison of the BMP alone group and the blank group by T test were both less than 0.05, while p value obtained through comparison of the ECM alone group and the BMP alone group was greater than 0.05. Compared to the blank group, the average bone rate of the ECM alone group and the BMP alone group increased by 8.3% and 10.8%, respectively. The above results indicated that the ECM alone and BMP alone both showed a significant regenerative effect for the amputated toe, and their effects were similar.

Mixed inducers of ECM and BMP were classified into 30, 60, 125, 250 and 500 (µg/mL) based on the concentration of BMP. The ECM gel was used at an amount of 0.25 mg/per toe (dry weight) and the BMP solution was used at a dose of 0.125 µL/per toe. A group added with 125 µg/mL of the BMP was named combination-125 group, and the other groups were named in the same way. For the combination-125 group, a dry weight ratio of the BMP to the ECM was 3:50,000, and an average bone rate was 83.0%, which increased by 31.3% compared to the blank group. Such results showed a significant synergistic effect produced by the combination of ECM and BMP. The regenerated bone mass induced by the mixed inducer of the ECM and the BMP increased with the increase of the BMP concentration, where a bone rate of the combination-250 group was 115.1%, which showed excessive bone regeneration; and a bone rate of the combination-500 group was 177.3%, which was about 3 times that of the ECM alone group (see FIG. 5).

2.3 Regeneration of Amputated Toes with Soft Tissues

In this model, the P2 bone was amputated at the middle, and the P2 bone distal to the amputation surface and all the P3 bone were removed, but soft tissues such as skin were remained to encapsulate the regeneration inducer which was simultaneously implanted. Thereafter, no treatment was performed until the mice were sacrificed 34 days after the implantation and the samples were collected for analysis. The experimental group, and the composition and amount of the inducer were the same as those in 2.2.

A bone rate of the combination-30 group was 101.4%, which showed excessive bone regeneration. The regenerated bone mass of the trauma model with soft tissue also increased with the increase of BMP concentration, but the increase was not obvious compared to the model without soft tissue. In addition, between the adjacent concentrations, significant difference was only observed between the combination-250 and the combination-500 (p=0.023). Except for the combination-500, the bone rate of each group in this model was greater than that of the corresponding group in the model with soft tissue. The bone rate of the combination-500 was about 1.5 times that of the ECM alone group (see FIG. 5). Such results demonstrated that the presence of soft tissues could significantly promote the regeneration of the phalange and the increase in BMP concentration led to different increases in the regeneration amount in different trauma models.

Example 3

1. ECM was obtained from a fresh pig small intestine, and the submucosa was separated by blunt machinery and then used to prepare an ECM lyophilized powder according to a reported method (Agrawal V, Johnson S A, Reing J. Epimorphic regeneration approach to tissue replacement in adult mammals. [J]. Proc Natl Acad Sci, 2010, USA 107: 3351-3355).

2. Recombinant human protein BMP-9 was purchased from Peprotech company (Catalog #120-07). BMP-9 was diluted to a concentration of 60 μg/mL with a diluent, and the diluent was a phosphate buffer (pH=7.2) containing 5% of trehalose. After BMP-9 was completely dissolved, hydroxyapatite micropowder was introduced to the diluted BMP-9 solution, where the hydroxyapatite micropowder was purchased from Ding'an Technology Co., Ltd. (Suzhou).

3. The use methods of the amputation model and the inducer were described as follows. One hind limb bone of a mouse was amputated at a proximal end of the ankle (see FIG. 6) to separate and remove all the bone tissues distal to the amputation surface. Part of the soft tissue was retained so that the soft tissue section was located approximately 3 mm distal to the bone section. After the natural hemostasis, the inducer was implanted into the remained soft tissue to expose to the damaged bone tissue and allow for the natural wound closure. Thereafter, no treatment was performed.

4. The method and results were described below. The ECM lyophilized powder was mixed with the diluted BMP-9 solution in an appropriate weight ratio, where a dry weight ratio of BMP to ECM was 3:100,000. In this example, the amount of the ECM lyophilized powder was 4 mg/per limb; the amount of the BMP solution was 2 μL/per limb; and the amount of the hydroxyapatite micropowder was 0.2 mg/per limb. After 45 days, the samples were collected for analysis, and the results showed that the regenerated bone was tightly bonded to the original bone, and the regenerated bone had a size of 3.98×1.86×3.04 mm (FIG. 6).

What is claimed is:

1. A method for bone regeneration in a subject having a severed digit or limb, consisting essentially of:
    i) preparing an extracellular matrix (ECM) gel, wherein the ECM gel is prepared by:
    lyophilizing ECM harvested from porcine urinary bladder tissue to obtain a lyophilized ECM powder; and
    dispersing the lyophilized ECM powder in a humid environment having a humidity greater than 85%, so that it gets damp and hydrated to form an ECM gel; and
    ii) administering an effective amount of the ECM gel as the only active ingredient to the subject in need thereof, wherein the ECM gel is implanted into a lesion of the severed digit or limb.

2. The method of claim 1, wherein the severed digit or limb has soft tissues remained.

3. The method of claim 1, wherein the severed digit or limb does not have soft tissues distal to the surface of the severed digit or limb, and wherein administering the ECM gel regenerates both of bone and soft tissues.

* * * * *